(12) United States Patent
Griffiths et al.

(10) Patent No.: US 10,136,947 B2
(45) Date of Patent: *Nov. 27, 2018

(54) SURGICAL PATIENT SIDE CART WITH DRIVE SYSTEM AND METHOD OF MOVING A PATIENT SIDE CART

(71) Applicant: INTUITIVE SURGICAL OPERATIONS, INC., Sunnyvale, CA (US)

(72) Inventors: Paul G. Griffiths, Santa Clara, CA (US); Arjang M. Hourtash, Santa Clara, CA (US); Paul W. Mohr, Mountain View, CA (US); David W. Robinson, Los Altos, CA (US); Nitish Swarup, Sunnyvale, CA (US); John W. Zabinski, Fremont, CA (US); Mark W. Zimmer, Fremont, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 185 days.

This patent is subject to a terminal disclaimer.

(21) Appl. No.: 14/808,639

(22) Filed: Jul. 24, 2015

(65) Prior Publication Data

US 2016/0022360 A1 Jan. 28, 2016

Related U.S. Application Data

(63) Continuation of application No. 14/209,239, filed on Mar. 13, 2014, now Pat. No. 9,101,348.
(Continued)

(51) Int. Cl.
*A61B 19/02* (2006.01)
*G05D 1/00* (2006.01)
(Continued)

(52) U.S. Cl.
CPC .......... *A61B 19/0248* (2013.01); *A61B 50/10* (2016.02); *A61B 50/13* (2016.02);
(Continued)

(58) Field of Classification Search
CPC .... B25J 5/00; B25J 5/007; B25J 5/008; A61B 19/0248; A61B 19/2203; A61B 2019/0254; A61B 2019/0252; A61B 2019/025

See application file for complete search history.

(56) References Cited

U.S. PATENT DOCUMENTS 5,746,282 A 5/1998 Fujiwara et al.
5,810,104 A 9/1998 Campbell
(Continued)

FOREIGN PATENT DOCUMENTS

JP H05286453 A 11/1993
JP 2010008204 A 1/2010

OTHER PUBLICATIONS

Extended European Search Report for Application No. 14770421.7, dated Sep. 15, 2016, 6 pages.
(Continued)

*Primary Examiner* — Jerrah Edwards
(74) *Attorney, Agent, or Firm* — Jones Robb, PLLC

(57) ABSTRACT

A patient side cart for a teleoperated surgical system can include at least one manipulator arm portion for holding a surgical instrument, a steering interface, and a drive system. The steering interface may be configured to detect a force applied by a user to the steering interface indicating a desired movement for the teleoperated surgical system. The drive system can include at least one driven wheel, a control module, and a model section. The control module may receive as input a signal from the steering interface corresponding to the force applied by the user to the steering
(Continued)

interface. The control module may be configured to output a desired movement signal corresponding to the signal received from the steering interface. The model section can include a model of movement behavior of the patient side cart, the model section outputting a movement command output to drive the driven wheel.

19 Claims, 8 Drawing Sheets

Related U.S. Application Data

(60) Provisional application No. 61/895,249, filed on Oct. 24, 2013, provisional application No. 61/791,889, filed on Mar. 15, 2013.

(51) Int. Cl.
   *B25J 5/00* (2006.01)
   *A61B 50/18* (2016.01)
   *A61B 50/10* (2016.01)
   *A61B 50/13* (2016.01)
   *A61B 34/30* (2016.01)

(52) U.S. Cl.
   CPC ............... *A61B 50/18* (2016.02); *B25J 5/007* (2013.01); *G05D 1/0011* (2013.01); *A61B 34/30* (2016.02); *A61B 2050/185* (2016.02)

(56) References Cited

U.S. PATENT DOCUMENTS

| | | | |
|---|---|---|---|
| 6,220,379 B1 | 4/2001 | Schugt et al. | |
| 6,227,320 B1 | 5/2001 | Eggert et al. | |
| 6,276,471 B1 | 8/2001 | Kratzenberg et al. | |
| 6,285,742 B1 | 9/2001 | Haumann et al. | |
| 6,422,241 B1 | 7/2002 | Soukal | |
| 7,017,689 B2 | 3/2006 | Gilliland et al. | |
| 7,076,830 B2 | 7/2006 | Conner et al. | |
| 7,080,703 B2 | 7/2006 | David et al. | |
| 7,090,042 B2 | 8/2006 | Coveyou et al. | |
| 7,273,115 B2 | 9/2007 | Kummer et al. | |
| 7,318,309 B2 | 1/2008 | Osborne | |
| 7,407,024 B2 | 8/2008 | Vogel et al. | |
| 7,530,412 B2 | 5/2009 | Heimbrock et al. | |
| 7,533,892 B2 | 5/2009 | Schena et al. | |
| 7,562,729 B2 | 7/2009 | Hammerle et al. | |
| 7,661,493 B2 | 2/2010 | Rose | |
| 7,831,292 B2 | 11/2010 | Quaid et al. | |
| 7,845,441 B2 | 12/2010 | Chambers | |
| 7,909,122 B2 | 3/2011 | Schena et al. | |
| 9,101,348 B2 * | 8/2015 | Griffiths | B25J 5/007 |
| 9,308,937 B2 | 4/2016 | Griffiths et al. | |
| 2007/0041817 A1 | 2/2007 | Kakinuma | |
| 2008/0287963 A1 | 11/2008 | Rogers et al. | |
| 2010/0169815 A1 | 7/2010 | Zhao et al. | |
| 2010/0180380 A1 | 7/2010 | Van Scheppingen et al. | |
| 2010/0243924 A1 | 9/2010 | Uchida et al. | |
| 2011/0087238 A1 | 4/2011 | Wang et al. | |
| 2011/0264108 A1 | 10/2011 | Nowlin et al. | |
| 2014/0107665 A1 | 4/2014 | Shellenberger et al. | |
| 2014/0316654 A1 | 10/2014 | Griffiths et al. | |
| 2015/0066050 A1 | 3/2015 | Jardine et al. | |
| 2016/0199143 A1 | 7/2016 | Griffiths et al. | |

OTHER PUBLICATIONS

English translation of JP2010008204A, 12 pages, [online], [retrieved on Jul. 1, 2015]. Retrieved from the Internet:< URL: http://translationportal.epo.org/emtp/translate/?ACTION=description-retrieval&COUNTRY=JP&ENGINE=google&FORMAT=docdb&KIND=A&LOCALE=en_EP&NUMBER=2010008204&OPS=jp.espacenet.com/ops&SRCLANG=ja&TRGLANG=en>.

International Search Report and Written Opinion for Application No. PCT/US14/26153, dated Aug. 14, 2014, 16 pages.

International Search Report and Written Opinion for Application No. PCT/US14/26374, dated Jul. 24, 2014, 15 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

SURGICAL PATIENT SIDE CART WITH DRIVE SYSTEM AND METHOD OF MOVING A PATIENT SIDE CART

This application is a continuation of U.S. application Ser. No. 14/209,239 (filed Mar. 13, 2014, now pending), which claims the benefit of U.S. Provisional Application No. 61/791,889, filed Mar. 15, 2013, and U.S. Provisional Application No. 61/895,249, filed Oct. 24, 2013, each of which is incorporated by reference herein in its entirety.

TECHNICAL FIELD

Aspects of the present disclosure relate to a teleoperated (robotic) surgical system patient side cart having a drive system for a user to maneuver the cart and methods of moving a patient side cart.

INTRODUCTION

The section headings used herein are for organizational purposes only and are not to be construed as limiting the subject matter described in any way.

Some minimally invasive surgical techniques are performed remotely through the use of teleoperated (robotically-controlled) surgical instruments. In teleoperated (robotically-controlled) surgical systems, surgeons manipulate input devices at a surgeon console, and those inputs are passed to a patient side cart that interfaces with one or more teleoperated surgical instruments. Based on the surgeon's inputs at the surgeon console, the one or more teleoperated surgical instruments are actuated at the patient side cart to operate on the patient, thereby creating a master-slave control relationship between the surgeon console and the surgical instrument(s) at the patient side cart.

A patient side cart need not remain stationary in a particular location, such as within one operating room, but instead may be moved from one location to another. For example, a patient side cart may be moved from one location to another, such as from one location in an operating room to another location in the same operating room. In another example, a patient side cart may be moved from one operating room to another operating room.

One consideration in moving a patient side cart of a teleoperated surgical system is the ease with which the patient side cart may be moved by a user. Due to its weight, size, and overall configuration, it may be desirable to provide a patient side cart that enables a user to move and maneuver the patient side cart with relative ease. It may further be desirable to configure a patient side cart that can be moved from one location to another in a safe manner.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a patient side cart for a teleoperated system comprises at least one manipulator arm portion for holding a surgical instrument, a steering interface, and a drive system. The steering interface may be configured to detect a force applied by a user to the steering interface indicating a desired movement for the teleoperated surgical system. The drive system may comprise at least one driven wheel, a control module, and a model section. The control module may receive as input a signal from he steering interface corresponding to the force applied by the user to the steering interface. The control module may be configured to output a desired movement signal corresponding to the signal received from the steering interface. The model section may comprise a model of movement behavior of the patient side cart, the model section outputting a movement command output to drive the driven wheel.

In accordance with at least one exemplary embodiment, a method of moving a patient side cart of a teleoperated surgical system, the patient side cart including a steering interface and a surgical instrument comprises the steps of: detecting a force applied to the steering interface with a sensor of the steering interface, transmitting an input corresponding to the applied force from the steering interface sensor to a drive system of the patient side cart, transmitting a desired movement command output based on the input corresponding to the applied force that is received from the steering interface, and transmitting a movement command output based on the desired movement signal and a modeled behavior of the patient side cart.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation. In the drawings.

DETAILED DESCRIPTION

Figure 1:
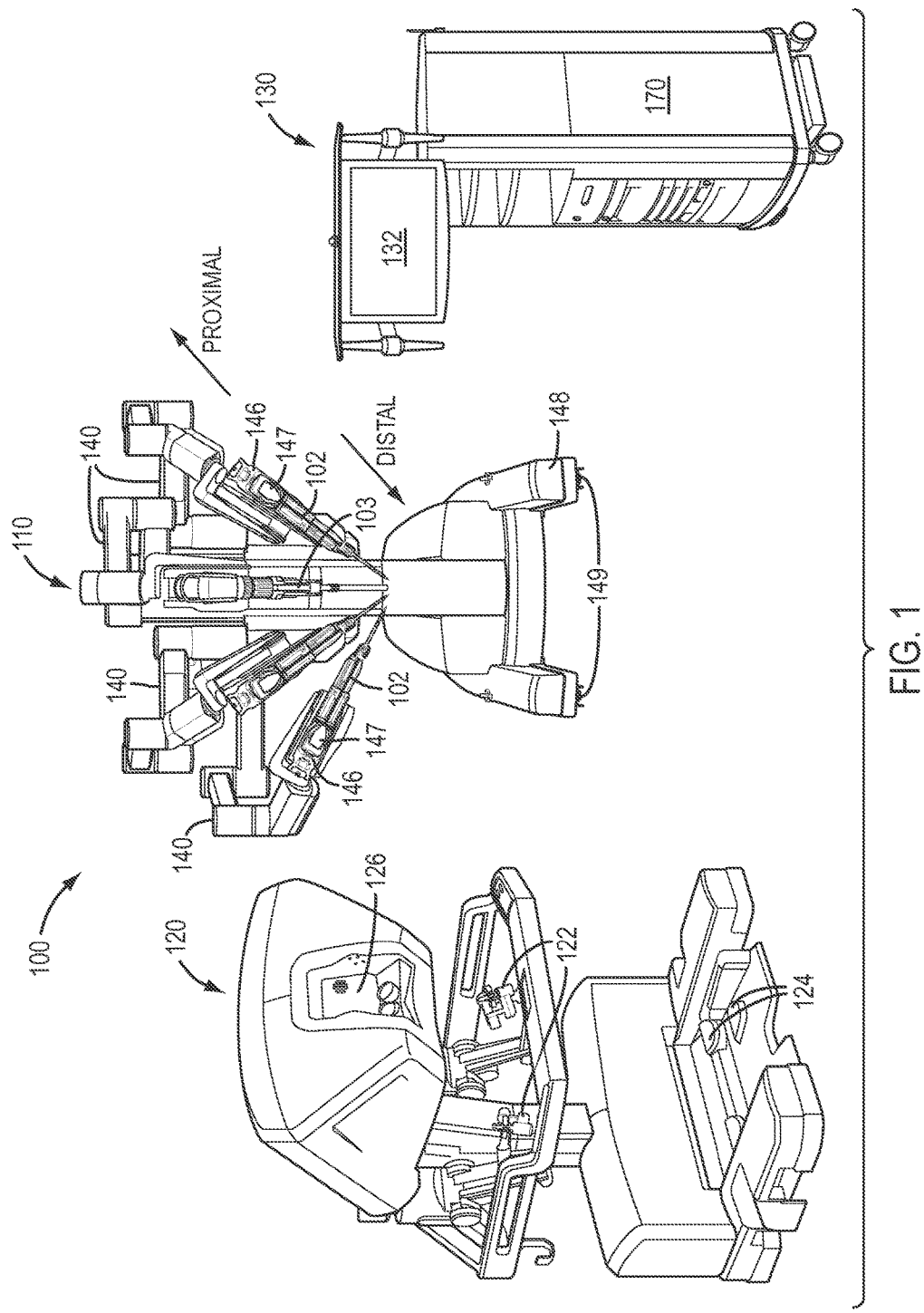
FIG. 1 is a diagrammatic view of an exemplary teleoperated surgical system in accordance with at least one exemplary embodiment.

This description and the accompanying drawings that illustrate exemplary embodiments should not be taken as limiting. Various mechanical, compositional, structural, electrical, and operational changes may be made without departing from the scope of this description and the invention as claimed, including equivalents. In some instances, well-known structures and techniques have not been shown or described in detail so as not to obscure the disclosure. Like numbers in two or more figures represent the same or similar elements. Furthermore, elements and theft associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

Various exemplary embodiments of the present disclosure contemplate a cart with a drive system and methods of roving a cart. Such a cart may be, for example, patient side cart of a teleoperated surgical system that includes a drive system. The drive system may include, for example, a control system that includes an inverse model of cart behavior. Further, the control system may include error correction, such as, for example, feedback control. The features of the exemplary embodiments described herein may be applied to other wheeled objects, such as, for example, imaging equipment, operating tables, and other wheeled devices.

A patient side cart of a teleoperated surgical system need not remain stationary in a particular location, such as within one operating room, but instead may be moved from one location to another. For example, a patient side cart may be moved from one location to another, such as from one location in an operating room to another location in the same operating room. In another example, a patient side cart may be moved from one operating room to another operating room.

Due to its size and the equipment and instrument that it may include, a patient side cart may have a considerable mass. For instance, a patient side cart may weigh from about 1000 pounds to about 2000 pounds, for example. In another example, an exemplary patient side cart may have a weight ranging from about 1200 pounds to about 1850 pounds. Furthermore, a patient side cart may be large in size. If a person were required to supply the force required to move a patient side cart, it may be difficult for the person to also steering the cart while providing the necessary motive force. Therefore, due to its weight, size, and overall configuration, it may be desirable to provide a patient side cart that enables a user to move and maneuver the patient side cart with relative ease. R may further be desirable to configure a patient side cart that can be moved from one location to another in a safe manner.

One way to address these issues is to provide a patient side cart with a system that provides a force to assist with moving the patient side cart. Such a system may be a drive system that includes one or more devices that drive or move a patient side cart so that a user need not provide all of the force necessary to move the cart. For instance, a drive system may provide all of the force necessary to move a patient side cart or a drive system may provide a large majority of the force necessary to move a patient side cart so that a user may sense the weight and/or handling of the cart when the user applies a force to move the cart.

A drive system for a patient side cart may interact with controls that a user operates to move the cart. To control the speed at which a patient side cart moves, the controls may include a throttle to provide an input to a drive system of the cart. In such a case, the controls may also include a brake to control stopping of the patient side cart. The controls would also require a steering device so that a user could indicate to the drive system what direction a patient side cart should be driven in. However, such an array of controls may be somewhat difficult for a user to operate, particularly if the user is not familiar with the controls. Therefore, it may be desirable to provide a patient side cart with a drive system and controls that are relatively easy to operate in a simple manner.

Various exemplary embodiments of the present disclosure contemplate a patient side cart of a teleoperated surgical system in which the patient side cart includes a steering interface for a user that operates in concert with a drive control system. One consideration in moving a patient side cart of a teleoperated surgical system is the ease with which the patient side cart may be moved by a user.

The steering interface may permit a user to move the patient side cart in a relatively easy and familiar manner without the use of multiple steering and drive interface devices. A steering interface in accordance with various exemplary embodiments may include "intelligence" in that they can enable the storage of various calibration data that can be provided to a control processor that uses drive control algorithms for motor-assisted driving of the cart. Such data may be used for various purposes, such as to calibrate devices of the steering interface which may vary to a degree from one to another. For instance, data could include calibration data for one or more sensors that are included in the steering interface. Calibration of a component of a steering interface, such as a force sensor, may include storing calibration data in a data storage device of the steering interface. The calibration may include, for instance, data that associates a force detected by a force sensor with a signal that a drive system of a cart may use to control movement of a cart. The calibration data may associate the detected force with a signal for a drive system through an algorithm, such as through one or more equations, look up tables, or other functions.

The intelligence functions of the steering interface may be configured to function automatically, such as when a steering interface is initially mounted to a cart and connections are made between the cart and steering interface to permit transmittal of data to the cart. For instance, the calibration function of a steering interface may function automatically when the steering interface is mounted to a cart, causing stored data from a calibration device of the steering interface to calibrate signals transmitted from one or more force sensors to a drive system of the cart.

In various exemplary embodiments, the steering interface may be replaceable, e.g., in the field, such as when the steering interface or component thereof is damaged or otherwise non-functional. In addition, if one or more components of a steering interface is damaged or otherwise requires repair, the steering interface could be removed so the component may be repaired or replaced. Recalibration could also be conducted on components of a steering interface once the steering interface has been removed so that the steering interface is ready to function when the steering interface is attached to a cart. According to an exemplary embodiment, a steering interfaces described herein may be used with various carts, including carts of different sizes and/or configurations. Further, various exemplary embodiments contemplate a steering interface for a patient side cart of a teleoperated surgical system.

Steering interfaces of the exemplary embodiments described herein may be provided in various forms. According to one exemplary embodiment, a steering interface for a patient side cart of a teleoperated surgical system may be provided in the form of a handlebar. However, the form or shape of the steering interface for a user of a patient side cart of a teleoperated surgical system is not limited to this exemplary embodiment. For example, a steering interface for a patient side cart may be in the form of a plurality of handlebars, one or more handles, a steering wheel, combinations of these interfaces, and other shapes and forms used for steering interfaces.

Teleoperated Surgical System

With reference to FIG. 1, a teleoperated surgical system 100 is provided which, in an exemplary embodiment, performs minimally invasive surgical procedures by interfacing with and controlling a variety of remotely operated surgical instruments, such as one or more surgical instruments 102, as those of ordinary skill in the art are generally familiar. The surgical instruments 102 may be selected from a variety of Instruments that are configured to perform various surgical procedures, and in accordance with various exemplary embodiments can have a variety of configurations to implement surgical procedures of conventional surgical instruments. Non-limiting examples of the surgical instruments 102 include, are but not limited to, instruments configured for suturing, stapling, cutting, grasping, applying electrosurgical energy (e.g., cautery energy), and a variety of other instruments with which those having ordinary skill in the art are generally familiar.

As illustrated in the schematic view of FIG. 1, the teleoperated surgical system 100 includes a patient side cart 110, a surgeon console 120, and a control cart 130. In non-limiting exemplary embodiments of the teleoperated surgical system, the control cart 130 includes "core" processing equipment, such as core processor 170, and/or other auxiliary processing equipment, which may be incorporated into or physically supported at the control cart 130. The control cart 130 may also include other controls for operating the teleoperated surgical system. As will be discussed in more detail below, in an exemplary embodiment, signal(s) or input(s) transmitted from surgeon console 120 may be transmitted to one or more processors at control cart 130, which may interpret the input(s) and generate command(s) or output(s) to be transmitted to the patient side cart 110 to cause manipulation of one or more of surgical instruments 102 and/or patient side manipulators 140a-140d to which the surgical instruments 102 are coupled at the patient side cart 110. It is noted that the system components in FIG. 1 are not shown in any particular positioning and can be arranged as desired, with the patient side cart 110 being disposed relative to the patient so as to affect surgery on the patient. A non-limiting, exemplary embodiment of a teleoperated surgical system with which the principles of the present disclosure may be utilized is a da Vinci® Si (model no. IS3000) commercialized by Intuitive Surgical, Inc. of Sunnyvale, Calif.

In general, the surgeon console 120 receives inputs from a user, e.g., a surgeon, by various input devices, including but not limited to, gripping mechanisms 122 and foot pedals 124, and serves as a master controller by which the instruments 102 mounted at the patient side cart 110 act as slaves to implement the desired motions of the surgical instrument(s) 102, and accordingly perform the desired surgical procedure. For example, while not being limited thereto, the gripping mechanisms 122 may act as "master" devices that may control the surgical instruments 102, which may act as the corresponding "slave" devices at the manipulator arms 140, and in particular control an end effector and/or wrist of the instrument as those having ordinary skill in the art are familiar with. Further, while not being limited thereto, the foot pedals 124 may be depressed to provide, for example, monopolar or bipolar electrosurgical energy, or to activate a variety of other functions (e.g., suction, irrigation, etc.) at the instruments 102.

In various exemplary embodiments, suitable output units may include, but are not limited to, a viewer or display 126 that allows the surgeon to view a three-dimensional image of the surgical site, for example, during the surgical procedure, e.g., via an optical endoscope 103 at the patient side cart 110. Other output units may include a speaker (or other component capable of transmitting sound), and/or a component with which a surgeon is in contact that can vibrate or the like to provide haptic feedback. In various exemplary embodiments, the one or more output units may be part of the surgeon console 120 and signals can be transmitted from the control cart 130 thereto. Although in various exemplary embodiments, one or more input mechanisms 122, 124 may be integrated into the surgeon console 120, various other input mechanisms may be added separately and provided so as to be accessible to the surgeon during use of the system, but not necessarily integrated into the surgeon console 120. In the context of the present disclosure, such additional input mechanisms are considered part of the surgeon console.

Thus, a "surgeon console" as used herein includes a console that comprises one or more input devices 122, 124 that a surgeon can manipulate to transmit signals, generally through a control cart such as 130 to actuate a remotely-controllable kinematic structure (e.g., surgical instruments 102 mounted at arms 140) at the patient side cart 110. The surgeon console 120 may also include one or more output devices that can provide feedback to the surgeon. As used herein, it should be understood, however, that a surgeon console can include a unit (e.g., substantially as shown by element 120 in FIG. 1) that integrates the various input and output devices, with, for example, a display, but also can include separate input and/or output devices that are in signal communication with the controllers, such as controllers provided at the control cart and accessible by a surgeon, although not necessarily integrated within a unit with various other input devices. As an example, input units may be provided directly at the control cart 130 and may provide input signals to a processor at the control cart. As such, a "surgeon console" does not necessarily require all of the input and output devices to be integrated into a single unit and can include one or more separate input and/or output devices.

The exemplary embodiment of FIG. 1 illustrates a patient side cart 110 with multiple, independently moveable manipulator arms 140 that each support an actuation interface assembly 146 and are configured to hold and manipulate various tools, including, but not limited to, for example, a surgical instrument 102, and an endoscope imaging device 103. However, those having ordinary skill in the art will appreciate that other patient side cart configurations may be used without departing from the scope of the present disclosure and claims.

Based on the commands input to input devices at, for example, the surgeon console 120, the patient side cart 110 can position and actuate the instrument(s) 102 to perform a desired medical procedure via the actuation interface assemblies 146 at the manipulator arms 140. The actuation interface assemblies 146 are configured to engage with transmission mechanisms 147 provided at a proximal end of the surgical instruments 102 (the general "proximal" and "distal" directions being shown in FIG. 1 relative to the surgical instrument). The surgical instrument 102 and the actuation interface assembly 146 may be mechanically and/or electrically connected to be able to operate the instrument 102. A patient side cart 110 may include a plurality of wheels 149 mounted or otherwise attached to the cart 110, such as to a base 148 of the cart 110.

The teleoperated surgical system 100 can include a control system that receives and transmits various control signals to and from the patient side cart 110 and the surgeon console 120. The control system can transmit light and process images (e.g., from an endoscope at the patient side cart 110) for display, such as, e.g., display 126 at the surgeon console 120 and/or on a display 132 associated with the control cart 130.

In exemplary embodiments, the control system may have all control functions integrated in one or more processors, such as a core processor 170 at the control cart 130, or additional controllers (not shown) may be provided as separate units and/or supported (e.g., in shelves) on the control cart 130 for convenience. The latter may be useful, for example, when retrofitting existing control carts to control surgical instruments requiring additional functionality, for example, by providing electrical energy for use in monopolar and bipolar applications.

One of ordinary skill in the art would recognize that the controllers, e.g., core processor 170, provided at control cart 130 may be implemented as part of a control system, which, as will be discussed in more detail below, controls various functions of the present disclosure. One of ordinary skill in the art would recognize that functions and features of the controllers, e.g., core processor 170, may be distributed over several devices or software components, including, but not limited to, processors at any of the surgeon console 120, patient side cart 110 and/or other devices incorporating processors therein. Functions and features of the control system, which may include core processor 170, may be distributed across several processing devices.

Due to the size and overall configuration of a patient side cart, including the jointed arms, possibly mounted with one or more surgical instruments, moving a patient side cart may require a significant exertion of effort and can be cumbersome for a user. Further, it may be challenging to move a patient side cart in a way in which it is relatively easy to control the movements and steering of the patient side cart, due to the weight and size of the patient side cart.

Figure 2:
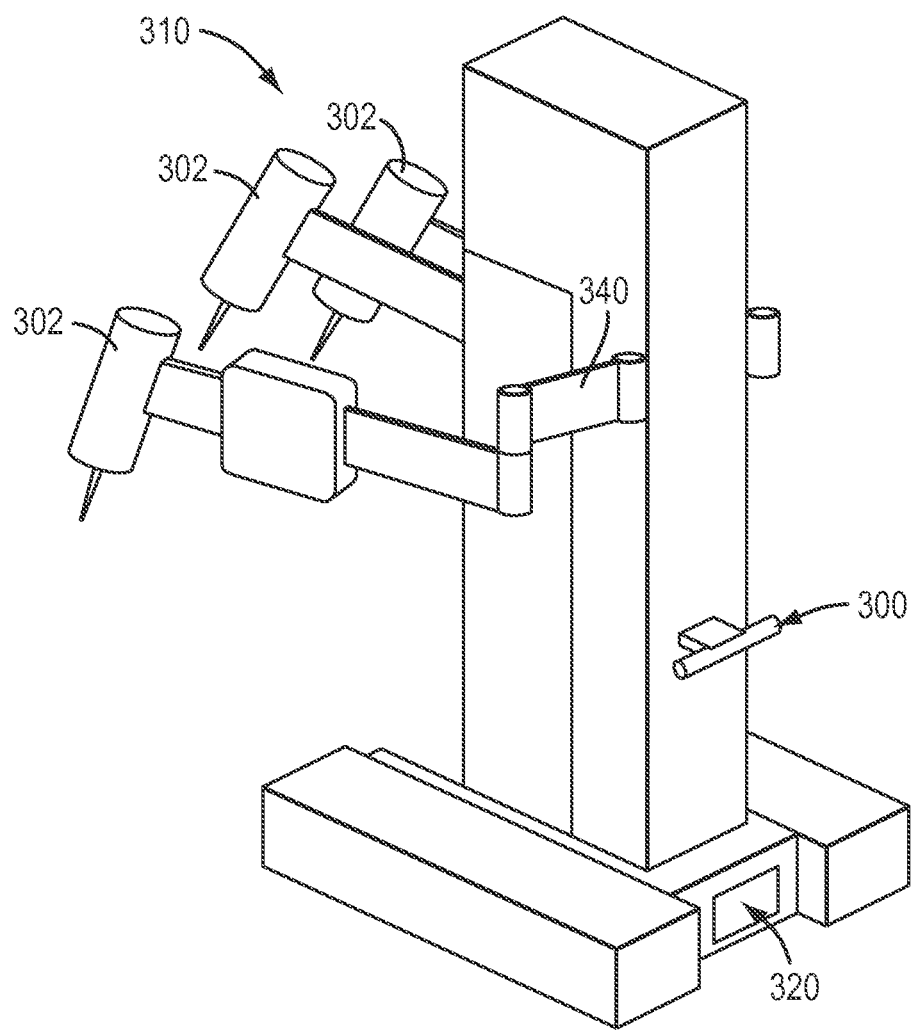
FIG. 2 is a schematic perspective view of an exemplary embodiment of a patient side cart that includes a steering interface.

Turning to FIG. 2, an exemplary embodiment of a patient side cart 310 is shown schematically. A patient side cart 310 may be arranged according to any of the exemplary embodiments described herein, such as with reference to FIG. 1 described above. For example, a patient side cart 310 may include one or more patient side manipulator(s) 340, which can also have one or more surgical instruments 302 installed thereat. A patient side cart 310 may include wheels (not shown) on its base to permit movement of the cart. For example, a patient side cart 310 may include three wheels or four wheels. One or more of the wheels may be driven by a drive system included in the patient side cart 310 that provides motive force to the driven wheel(s), as will be discussed below.

According to an exemplary embodiment a patient side cart may include a steering interface that receives input from a user indicating what direction the user would like the patient side cart to move in. In addition, the steering interface may receive input from a user indicating at what speed the user would like the patient side cart, such as by detecting the amount of force a user applies to the device.

According to an exemplary embodiment, a patient side cart 310 of a teleoperated surgical system may include a steering interface 300, as shown in FIG. 2. In one exemplary embodiment, a steering interface 300 may be configured as described in U.S. application Ser. No. 14/208,663 , filed on Mar. 13, 2014 and claiming priority to U.S. Provisional Application No. 61/791,924 entitled "Surgical Patient Side Cart with Steering Interface" and filed on Mar. 15, 2013 , each of which is hereby incorporated by reference in its entirety. However, steering interfaces having other configurations also can be employed in conjunction with the drive and control systems according to exemplary embodiments of the present disclosure. A steering interface 300 may be used to detect forces applied by a user to the steering interface 300, which in turn may issue a signal to a controller of a drive system of a patient side cart 310, which causes the patient side cart 310 to be driven and steered in a desired manner. As shown in the example of FIG. 2, a steering interface 300 may be attached to a rear of a patient side cart 310, with one or more manipulator arms 302 being located at a front of the patient side cart 310. However, the exemplary embodiments described herein are not limited to a patient side cart 310 with a steering interface 300 attached to a rear, and the steering interface 300 may instead be mounted on other portions of a patient side cart 310, such as a front or side of the patient side cart 310.

Drive System

Information received at a steering interface may be used by a drive system of a patient side cart to provide motive force to one or more transportation mechanisms of the cart. According to an exemplary embodiment, a patient side cart may include one or more wheels as transportation mechanisms to move the cart in a desired direction. One or more of the wheels may be driven according to commands issued from the drive system of the patient side cart.

Figure 3:
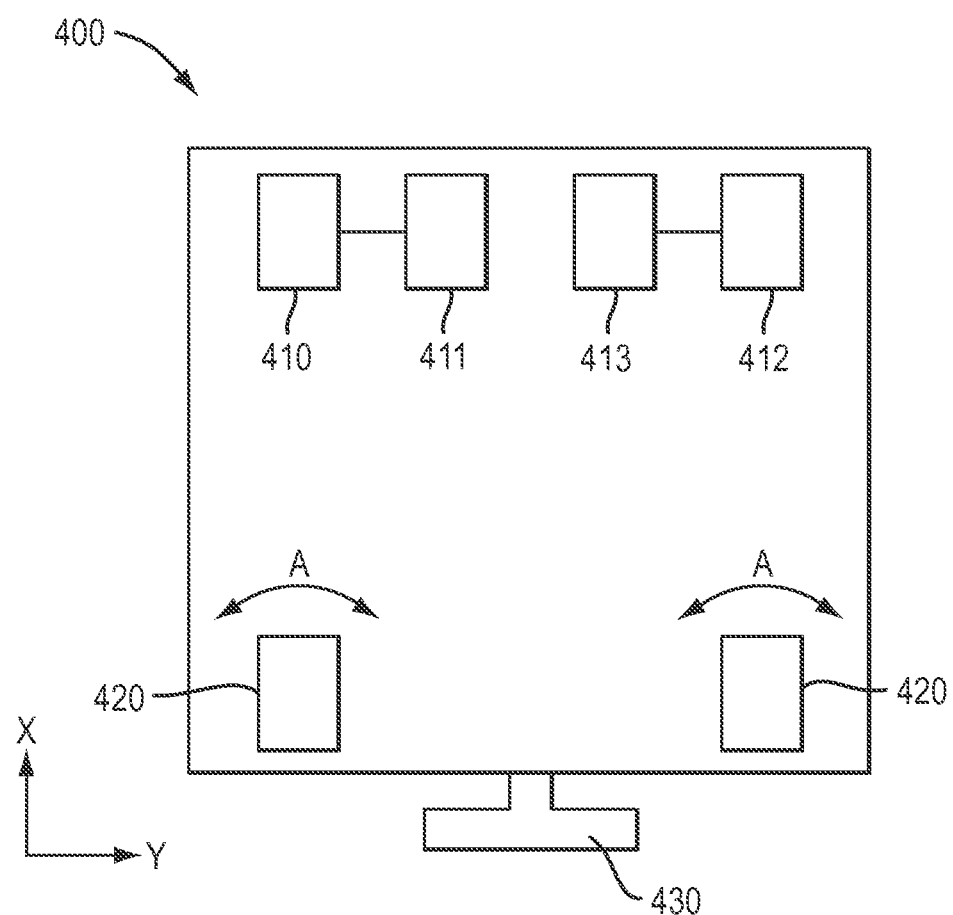
FIG. 3 is a plan schematic view of an exemplary embodiment of a wheel arrangement of a patient side cart with a steering interface.

Turning to FIG. 3, a top schematic view of an exemplary embodiment of a wheel arrangement for a patient side cart 400 is shown. A patient side cart 400 may include one or more front wheels 410, 412 and one or more rear wheels 420, as shown in FIG. 3. The front of a patient side cart 400 may be, for example, where manipulator arms are positioned. Thus, wheel 410 may be a front left wheel 410 while wheel 412 may be a front right wheel 412.

According to an exemplary embodiment, one or more wheels of a patient side cart 400 may be driven. In one exemplary embodiment, the front wheels 410, 412 of a patient side cart 400 of FIG. 3 may be driven while rear wheels 420 are not driven. According to an exemplary embodiment, driven wheels may be individually driven by separate motors. For instance, motors 411, 413 may be provided to respectively drive wheels 410, 412. Further, motors 411, 413 may drive wheels 410, 412 independently. In other examples, wheels in the rear of a patient side cart may be driven or all wheels of a patient side cart may be driven. Wheels that are driven may be fixed so that the wheels are prevented from turning. According to another embodiment driven wheels may be permitted to turn, either freely or in a controlled manner.

Figure 4:
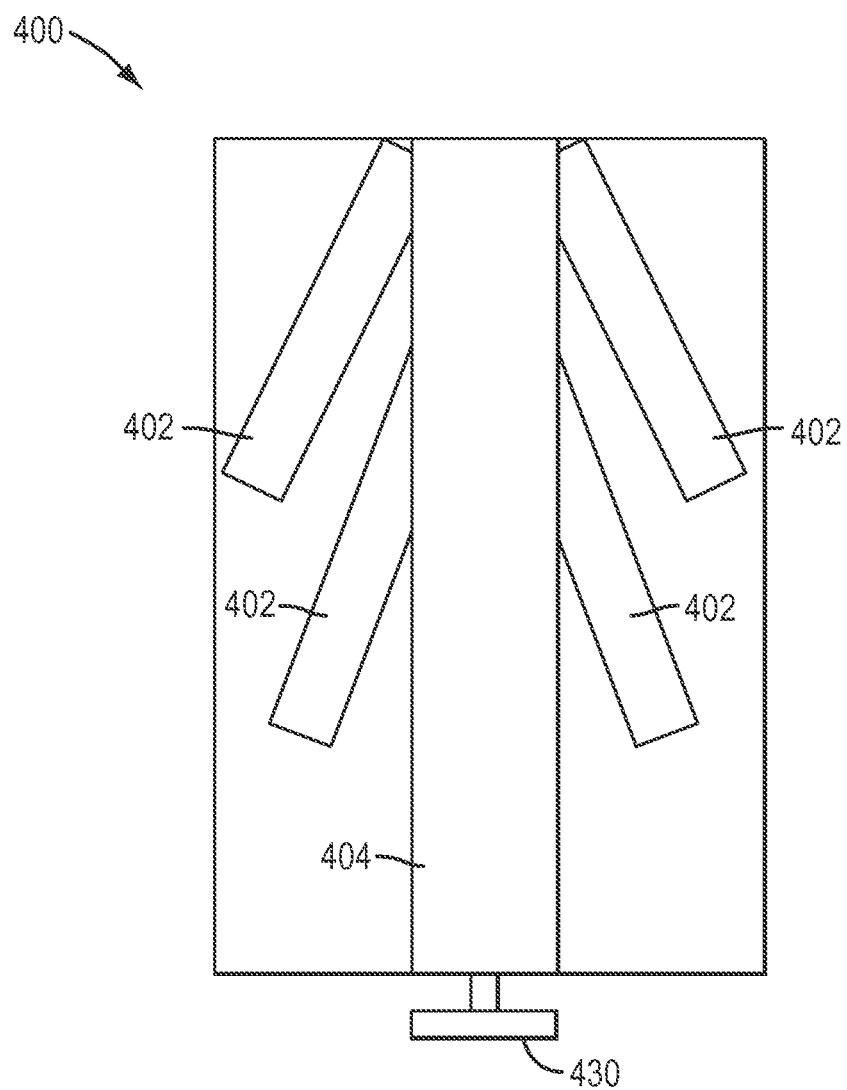
FIG. 4 is schematic top view of an exemplary embodiment of a patient side cart in a stowed configuration.

Wheels of a cart may be driven to produce a speed of, for example, approximately 1 meter per second when the manipulator arms of the cart are in a stowed, retracted position. Turning to FIG. 4, an exemplary embodiment of a patient side cart 400 is shown in a stowed configuration. A patient side cart 400 may include a steering interface 430 and a plurality of manipulator arms 402 holding surgical instruments (not shown), such as according to the embodiments of FIG. 1. In the stowed configuration shown in the example of FIG. 4, the manipulator arms 402, and any respective instruments and other components installed thereon, may be folded into a relatively compact arrangement toward a center of the patient side cart 400. Further, a post 404 upon which the manipulator arms 402 may be mounted may be in a non-extended, compact configuration as well. Those having ordinary skill in the art would be familiar with various exemplary embodiments of patient side carts having in which, for example, a central support post from which one or more of the passively jointed manipulator arms extend is provided in a telescoping arrangement so as to be raised and lowered relative to the base of the cart. In a stowed configuration, therefore, the post can be in the lowered, non-extended positron and the manipulator arms can be positioned toward each other and proximate to a center portion of the cart.

According to an exemplary embodiment, a wheel that is not driven may be permitted to spin freely as the patient side cart is driven and the wheel contacts a ground surface. For instance, rear wheels 420 of a patient side cart 400 may be permitted to turn in direction A indicated in FIG. 3. According to an exemplary embodiment, one or more wheels may have a configuration similar to a caster wheel and may be permitted to turn freely about a vertical axis so that a wheel may turn in a left and right direction as a patient side cart changes direction. For instance, rear wheels 420 in FIG. 3 may have a configuration similar to a caster wheel and be permitted to turn freely about a vertical axis. Such wheels may also spin freely so that when a patient side cart is driven, freely spinning wheels in contact with a ground surface also move. Wheels may also be turned by steering mechanisms, such as linkages and/or motors, according to steering input provided by a user.

Thus, according to one exemplary embodiment, a patient side cart 400 may include front wheels 410, 412 that are driven and rear wheels 420 that are not driven but are permitted to freely turn, as shown in FIG. 3. In other words, the wheels of a patient side cart 400 may have a configuration and arrangement opposite to those of a shopping cart commonly used in grocery stores and other retailers wherein the rear wheels (e.g., disposed proximate to the handle of the shopping cart) are driven and the front wheels are castered. A patient side cart 400 with a configuration such as in the exemplary embodiment of FIG. 3 can minimize or avoid relatively large sweeping motions, in particular at the front of the cart opposite to where the steering interface is positioned. Minimizing such large sweeping motions at the front of the cart provides the user with greater control in maneuvering the cart and minimizes the risk of collisions with the cart at the front of the cart where visibility by a user may be limited as a user maneuvers the cart from the rear end of the cart proximate the rear wheels 420.

As discussed above, when desiring to move the patient side cart 400, a user may engage a steering interface 430 of a patient side cart 400 and impart a force to the steering interface 430 to indicate which directions the user desires the patient side cart 400 to move in. For example, a user may push the steering interface 430 in the fore direction (relative to the front wheels 410, 412 and the rear wheels 420) along direction X in FIG. 3 or may pull the steering interface 430 backwards in the aft direction along direction X in FIG. 3 to indicate a desire to move a patient side cart 400 either forward or backward.

In addition, a user may apply a force having at least a component in the Y direction of FIG. 3 to indicate a desire to a turn the patient side cart either to the left or right (relative to the front wheels 410, 412 and the rear wheels 420 of the patient side cart 400). Forces applied in the Y direction indicating a desire to turn a patient side cart 400 may be used to provide a yaw control of the patient side cart 400 and control turning of the cart 400. For instance, a user may apply a lateral force to a steering interface 430 along directions substantially perpendicular to the forward and rearward directions of FIG. 3, which may substantial y correspond to a direction along a Y direction or axis. The sensor configuration discussed above for detection of a force applied by a user to indicate a desired movement for a patient side cart is one exemplary way of sensing turning (e.g., yaw) and fore/aft steering control, but other techniques also could be employed and sensor configurations modified accordingly. For instance, according to another exemplary embodiment, a user may indicate that the patient side cart should turn by applying more force to one of a left portion and right portion of the steering interface 430, in relation to a left-right direction extending along the Y axis in FIG. 3, than the other of the left portion and the right portion. The steering interface 430 may be configured to detect the applied forces and issue a signal to the control system of the drive system, which commands the drive system to turn in the direction desired by the user.

A patient side cart may include a drive system configured to receive signal(s) from a steering interface (e.g., from one or more sensors at the steering interface). A patient side cart may include a control system or controller, which may be part of the drive system or a separate device or system in communication with the drive system. Referring again to FIG. 3, for example, the control system may be configured to receive signal(s) or input(s) from a steering interface 430 of a patient side cart 400 and, based upon the received input(s), issue one or more command outputs or outputs to control the driven wheel(s) of the patient side cart 400, such as the driven front wheels 410, 412 shown in FIG. 3. For example, a command output issued by the control system for the drive system of a patient side cart may be a command output to drive a wheel to move the cart in a forward or backward direction, and/or a command output to drive a wheel in a way to provide a yaw rate and turn the cart in a direction desired by a user.

Figure 5:
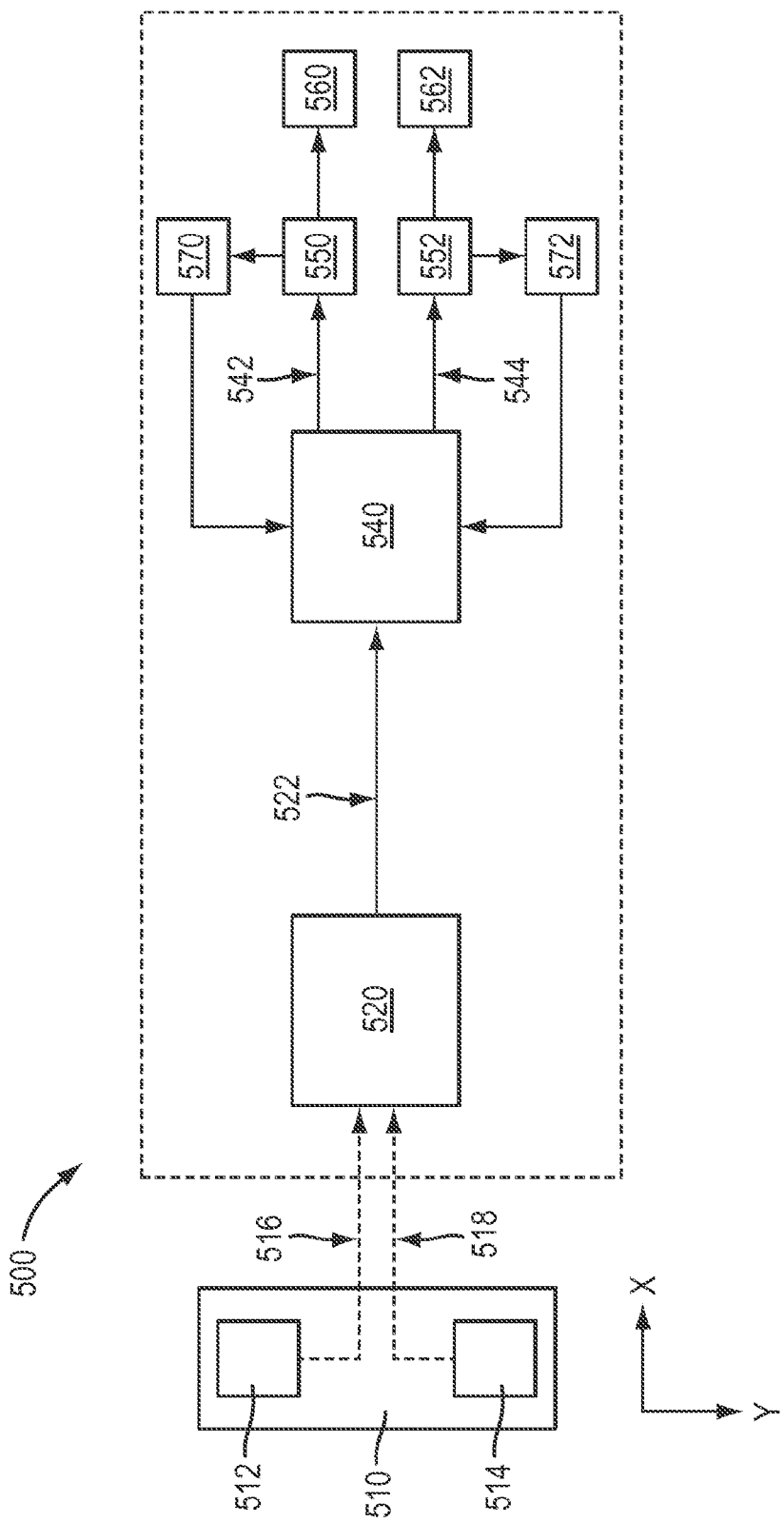
FIG. 5 is a schematic block diagram of an exemplary embodiment of a drive system for a patient side cart.

Turning to FIG. 5, a schematic block diagram of one exemplary embodiment of a drive system 500 for a patient side cart is shown in communication with a steering interface 510. A steering interface 510 may be configured as a handlebar according to the embodiments described above for the steering interface 430 of FIG. 3, for example. For an exemplary steering interface that can be used in conjunction with the Reference is made to U.S. application Ser. No. 14/208,663, filed on Mar. 13, 2014 and claiming priority to U.S. Provisional Application No. 61/791,924 entitled "Surgical Patient Side Cart with Steering Interface" and filed on Mar. 15, 2013, each being incorporated by reference herein in its entirety. The steering interface 510 may include one or more sensors to detect forces applied by a user to indicate a desired movement for a patient side cart. That is, as described above, the steering interface can include one or more sensors for sensing push/pull and turning forces indicating a desire to move the cart in the fore/aft and left/right directions.

In the exemplary embodiment illustrated in FIG. 5, the steering interface 510 includes a first sensor 512 and a second sensor 514 that detect forces along the X and Y directions (as shown in FIGS. 3 and 5). In various exemplary embodiments, the sensors 512 and 514 can be load cells. In an exemplary embodiment, the sensors 512 and 514 can be configured as those disclosed for use in the steering interface described in U.S. application Ser. No. 14/208,663, filed on Mar. 13, 2014 and claiming priority to U.S. Provisional Application No. 61/791,924 entitled "Surgical Patient Side Cart with Steering Interface" and filed on Mar. 15, 2013 each of which is incorporated by reference herein in its entirety.

The steering interface 510 may issue or transmit a first input or signal 516 from the first sensor 512 and a second input or signal 518 from the second sensor 514, which are received by the drive system 500 of a patient side cart that the steering interface 510 is attached to. First input 516 and second input 518 may include information about forces applied by the user to the steering interface 510 to indicate a desired movement, For instance, first input 516 and second input 518 may each include data corresponding to a force detected in the X direction of FIG. 5 data, such as $F_x$ data that will be discussed below, and data corresponding to a force detected in the Y direction of FIG. 5, such as $F_y$ data that will be discussed below.

Although first input 516 and second input 518 may be provided separately, as shown in FIG. 5, first input 516 and second input 518 may be combined or otherwise provided as a single input. Furthermore, although each of first input 516 and second input 518 may include both data for forces directed in the X direction and Y direction of FIG. 5, such as $F_x$ data and $F_y$ data, first input 516 and second input 518 may instead be processed so that one input includes only $F_x$ data and the other input includes only $F_y$ data when more than one input is provided.

According to an exemplary embodiment, a steering interface 510 may include a plurality of sensors, such as the first sensor 512 and the second sensor 514 shown in FIG. 5, so that information from the sensors may be combined or compared to determine a desired motion indicated by a user. For instance, $F_y$ data from the first sensor 512 and from the second sensor 514 may be analyzed by the drive system 500 to determine if a user is applying a force to the steering interface 510 along the Y direction to indicate a desire to turn a patient side cart. When the $F_y$ data indicates a user's desire to turn a patient side cart, a command output may be issued to cause the patient side cart to turn. $F_x$ data from the first sensor 512 and from the second sensor 514 may be similarly analyzed by the drive system 500 to determine a user's desire to move a patient side cart in a fore/aft direction, such as along the X direction.

According to an exemplary embodiment, a patient side cart may include one or more devices to condition signals received from a steering interface so that the signals may be further processed. As shown in FIG. 5, a drive system 500 may include a signal conditioner 520, which may include one or more devices with which those of ordinary skill in the art have familiarity. For instance, signal conditioner 520 may include an amplifier to increase the power of signals 516, 518. Signal conditioner 520 also may include an analog-to-digital converter to convert analog signals 516, 518 to a digital form for further processing. Signal conditioner 520 may include these devices in combination with one another. Once signals 516, 518 have been conditioned by signal conditioner 520, the signals may be sent via a high speed communication connection 522 to other components of the drive system 500. In a non-limiting example, the high speed communication connection 522 may be an RS422 type of connection.

Drive system 500 may further include a control system or controller 540, according to an exemplary embodiment. Control system 540 may be configured to receive signal(s) (which may be first conditioned and processed by signal conditioner 520) from a steering interface 510 indicating a desired movement for a patient side cart, to analyze the received signals, and to issue one or more command outputs to cause the patient side cart to move in the desired manner.

According to an exemplary embodiment, control system 540 may issue a separate command output for each driven wheel to effect a desired movement for a patient side cart. For instance, if a patient side cart has a first driven wheel 560 and a second driven wheel 562, control system 540 may issue or transmit a command output 542 for first driven wheel 560 and a command output 544 for second driven wheel 562. First driven wheel 560 may be, for example, a front left wheel, such as the front left wheel 410 of the patient side cart 400 of FIG. 3, while second driven wheel 562 may be, for example, a front right wheel, such as the front right wheel 412 of the patient side cart 400 of FIG. 3.

According to an exemplary embodiment, drive system 500 may include one or more devices to cause a desired movement of driven wheels 560, 562. For example, drive system 500 may include one or more devices 550, 552 that cause wheels 560, 562 to move according to command outputs 542, 544 issued from the control system 540. According to various exemplary embodiments, drive devices 550, 552 can be motors, although other types of devices familiar with those of ordinary skill in the art to cause wheel motion according to a command output also can be utilized. According to an exemplary embodiment, each driven wheel may be provided with its own drive device so that each driven wheel is independently driven. As shown in FIG. 5, first driven wheel 560 may be driven by a first drive device 550 and second driven wheel 562 may be driven by a second drive device 562.

A drive system for a patient side cart may include sensors and controls to sense a movement of the cart, compare that movement with a movement desired by a user, and adjust the movement of the cart accordingly. According to an exemplary embodiment, a drive system 500 can be configured to detect movement of a patient side cart and provide the detected movement to the drive system 500 for possible correction. The detected movement may be used, for instance, in a feedback type of control. Movement of the cart may be detected indirectly, such as by detecting information from various components that affect movement of the cart. For example, as shown in FIG. 5, a first sensor 570 may be used to detect the movement of the drive device 550 that drives driven wheel 560 and a second sensor 572 may be used to detect the movement of the drive device 552 that drives driven wheel 562.

Signals from sensors 570, 572 may be sent to control system 540 and analyzed to determine the speeds of driven wheels 560, 562. The control system 540 can calculate a turning rate of a patient side cart, which can be determined on the basis of a difference in speed between the first driven wheel 560 and the second driven wheel 562. According to an exemplary embodiment, the information detected by sensors 570, 572 may be used by control system 540 in a feedback arrangement. However, the embodiments described herein are not limited to a feedback control scheme but instead may use other control schemes such as, for example, a feed forward control scheme may be used in one or more control blocks of the overall scheme. According to another exemplary embodiment, a drive system 500 may include other types of sensors to determine the movement of a patient side cart, such as an accelerometer and/or sensors that detect other components of the cart, such as a wheel or axle rotational speed. Further, the drive system 500 may be configured to minimize or eliminate deadbands so the drive system 500 is responsive, with little to no delay between the force applied by a user to a steering interface and a desired movement of a patient side cart. For instance, the components of a drive system 500 and/or steering interface 510 may be include high quality, responsive components or may be otherwise configured to minimize any delay in their responsiveness.

According to an exemplary embodiment, control system 540 may limit the speed of a patient side cart on a basis of the configuration of the cart. Control system 540 may analyze one or more signals indicating a desired movement of a patient side cart and issue one or more command outputs 542, 455 to driven wheels 560, 562 on a basis of the configuration of the cart. For instance, if a patient side cart is in stowed configuration, such as in the exemplary embodiment of FIG. 4, control system 540 may permit a patient side cart to travel at a speed and/or acceleration desired by a user or limit the desired speed and/or acceleration by a small degree. Conversely, if the patient side cart is not in a stowed configuration, such as when manipulator arms are extended, control system 540 may limit a desired speed and/or acceleration by a greater amount than when the cart is in the stowed configuration. The limitation on speed and/or acceleration may be imposed to minimize instability during travel of a cart. According to an exemplary embodiment, a first maximum speed and/or acceleration may be imposed by control system 540 when a patient side cart is in a stowed configuration and a second maximum speed and/or acceleration may be imposed when the cart is in a non-stowed configuration, with first maximum speed and/or acceleration being greater than the second maximum speed and/or acceleration. However, the exemplary embodiments are not limited to two maximum speeds and/or accelerations but instead may provide various maximums, such as varying the maximum speed and/or acceleration on a basis of the configuration of a cart, such as an extent to which the components of the cart, such as manipulator arms, are extended. Thus, control system 540 may control and limit a desired speed and/or acceleration for a patient side cart so that the cart travels at lower speeds and/or accelerations when the cart is in non-stowed configurations with extended manipulator arms than when the cart is in a stowed configuration with retracted manipulator arms.

According to an exemplary embodiment, a patient side cart may include one or more sensors to determine the configuration of a patient side cart. For instance, one or more sensors may detect the position of manipulator arms and provide signal(s) to control system 540 about the manipulator arm positions. Position sensor(s) may be, for example, proximity sensors, encoders connected to components of a patient side cart, such as manipulator arm motors, and other position sensors used by one of ordinary skill in the art. Control system 540 may use the signal(s) to determine what degree, if any, to limit a speed and/or acceleration of a patient side cart. Other methods may be used to determine the position of components of a patient side cart. For instance, commands sent to drive motors of cart components, such as the drives for manipulator arms, may be used to predict the location of the components, input from a user providing information on the configuration of a cart may be used to determine a state of the cart, and other location determining methods used in the art may be utilized. Further, the positions other components besides manipulator arms may be detected when determining the configuration of a cart and to what degree a desired speed and/or acceleration should be limited.

Figure 6:
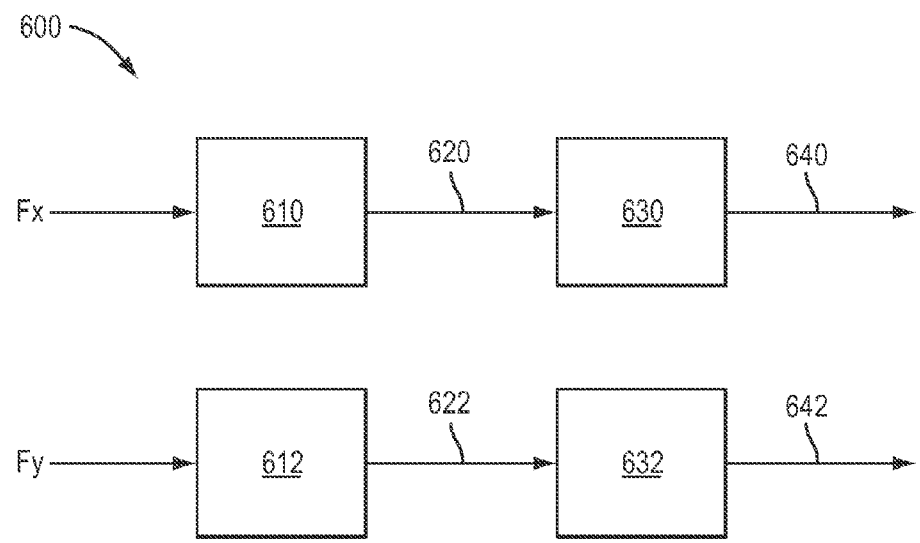
FIG. 6 is a schematic block diagram of an exemplary embodiment of a control system of a drive system for a patient side cart.

Turning to FIG. 6, a schematic block diagram for an exemplary embodiment of a control system 600 for a drive system of a patient side cart is shown. Control system 600 may be used, for example, as the control system 540 shown in FIG. 5. Control system 600 may receive one or more inputs or signals from a steering interface, such as the steering interface 510 of FIG. 5. For instance, if a steering interface 510 includes one or more sensors to measure forces applied by a user in the X and Y directions of FIG. 5, the sensors may detect the forces and issue signals corresponding to the forces. These signal(s) or input(s) may be received by a control system 600, which in turn may output command outputs to drive wheels driven by the drive system.

For instance, a control system 600 may receive a signal or input $F_x$, which may correspond to the force applied to the steering interface 510 in the X direction of FIG. 5. Control system 600 may also receive a signal or input $F_y$, which may correspond to the force applied to the steering interface 510 in the Y direction of FIG. 5. For example, in the exemplary embodiment wherein steering interface 510 includes a plurality of sensors 512, 514, as shown in FIG. 5, input $F_x$ and input $F_y$ may represent inputs or signals from the plurality of sensors to indicate movements along the X direction and the Y direction, respectively, that are desired by a user of a patient side cart. As shown the exemplary embodiment of FIG. 5, input $F_x$ and input $F_y$ may be provided separately. In another embodiment, input $F_x$ and input $F_y$ may be provided as a single input or signal. Further, each of input $F_x$ and input $F_y$ may be provided as combined inputs from a plurality of sensors of a steering interface (such that input $F_x$ includes data from multiple sensors and input $F_y$ includes data from multiple sensors), or separate $F_x$ and $F_y$ inputs may be provided from each sensor of a steering interface.

A control system may include one or more control modules configured to receive an input signal, such as a signal from a steering interface, and output a desired behavior. The desired behavior may be, for example, a desired overall movement for the patient side cart and/or may be desired individual movements for the driven wheels of a patient side cart. For instance, a signal corresponding to a force applied to a steering interface by a user can be analyzed and an output of a desired movement may be provided. The desired movement of the cart may correspond to the force applied to the steering interface. An output of a desired movement may represent, for instance, a desired velocity and/or acceleration for a patient side cart. The input signal may be first conditioned and/or processed, such as by signal conditioner 520 of FIG. 5, before being converted to a desired behavior by a control module. The desired behavior may be, for example, one or more of a desired velocity, acceleration, and yaw (turning) rate.

According to an exemplary embodiment, a control system 600 may include a first control module 610 and a second control module 612, as shown in FIG. 6. First control module 610 may be configured to receive signal $F_x$, which may correspond to the force applied to the steering interface 510 in the X direction of FIG. 5, analyze signal $F_x$, and output a desired fore/aft movement signal 602 along the X direction. Second control module 612 may be configured to receive signal $F_y$, which may correspond to the force applied to the steering interface 510 in the Y direction of FIG. 5, analyze signal $F_y$, and output a desired yaw rate signal 622 for a patient side cart to effect turning of the cart. The desired fore/aft movement signal 620 and the desired yaw rate signal 622 may correspond to a desired velocity and/or acceleration along the X and Y directions, respectively.

To perform the actions of analyzing input signals $F_x$, $F_y$, and generating desired movement signals, control modules 610, 612 may include information that correlates forces applied to a steering interface along the X and Y directions to desired movements of the patient side cart in the X and Y directions. For example, control modules 610, 612 may include maps, algorithms, look-up tables, or other functions used in the art to correspond a force input to a steering interface to a desired movement of a patient side cart, such as a desired velocity and/or desired acceleration. According to an exemplary embodiment, control modules 610, 612 may include one or more damping parameters to affect the output of control modules 610, 612 in a desired manner, such as to control the variation of the output of control modules 610, 612 over time.

Once a signal corresponding to a desired movement, such as a desired velocity and/or desired acceleration, has been provided, a command output that corresponds to the desired movement can be output. For example, components of a drive system, such as a motor driving a driven wheel, may not be configured to receive a desired movement signal that is in form of a desired velocity and/or desired acceleration and cause the desired movement of the cart without the desired movement signal being in the form of a force or a torque. In other words, a motor driving a driven wheel might be configured to receive a command signal that is in the form of a force (or a torque, which could be interpreted by static scaling, for example) instead of in the form of a velocity and/or an acceleration, which the motor might not be capable of interpreting. Thus, desired movement signals represent an action or output that a component, such as a motor for a driven wheel, should perform as opposed to instructions or command outputs input to the motor to cause the desired movement. To achieve the desired movement, a control system may include one or more model sections configured to produce command outputs, such as, for example, command outputs corresponding to a force or torque, that are based on signals corresponding to a desired movement. The command outputs (e.g., in the form of a force or a torque) may be issued to components of a drive system that cause movement, such as a motor for a driven wheel.

Turning to FIG. 6, control system 600 may include a fore/aft model section or module 630 configured to receive a desired raw fore/aft movement signal or input 620, analyze the signal, and issue or transmit a fore/aft command output 640 corresponding to the desired movement. Fore/aft command output 640 may be, for example, a command output to a motor to drive a driven wheel in a way that will produce the desired fore/aft movement. For instance, fore/aft command output 640 may be in the form of a force or a torque command for a motor that drives a driven wheel. Control system 600 may also include a yaw mod& section or module 632 configured to receive a desired raw yaw signal or input 622, analyze the signal, and issue or transmit a yaw rate command output 642 corresponding to the desired yaw rate for turning a patient side cart. Yaw rate command output 642 may be in the form of a differential velocity between driven wheels or a torque command for motors that drive driven wheels. Thus, yaw rate command output 642 may be, for example, a command output to motors of a drive system to produce a torque that will cause a patient side cart to turn in a desired manner. For example, if a drive system 500 includes a first driven wheel 560 and a second driven wheel 562, yaw rate command output 642 may cause the driven wheels 560, 562 to rotate at different speeds to produce an overall torque for a patient side cart that will cause the cart to turn.

According to an exemplary embodiment, model sections 630, 632 can be separate sections or modules of a control system 600, as shown in FIG. 6, or may be a single section or module (not shown).

First command output 640 and second command output 642 may be further processed to provide particular command outputs for individual driven wheels. For example, if a patient side cart has a first driven wheel 560 and a second driven wheel 562, as shown in FIG. 5, first command output 640 and second command output 642 may be further processed by control system 600 to provide separate command outputs 542, 544 for first driven wheel 560 and second drive wheel 562, as shown in FIG. 5. Command outputs 542, 544 may be the same or may differ, depending upon the desired movement for a patient side cart and the command outputs for driven wheels 560, 562 that effect the desired movement.

To convert a desired movement of a patient side cart, such as a desired velocity and/or acceleration, into command outputs for operation of the drive system, such as a force or a torque command for a motor, model sections 630, 632 of a control system 600 may include models configured to receive an incoming signal, such as the desired fore/aft signal 620 and he desired yaw rate signal 622, and issue a command output to cause a patient side cart to move in a desired manner. According to an exemplary embodiment, a model may correlate a desired movement to a command output for causing the desired movement, for example, by accounting for the kinematics of a patient side cart, such as the mass and configuration of cart. A map, algorithm, functional equation, look-up table, or other technique with which those of ordinary skill in the art would understand can be used to convert a signal indicative of a desired motion, such as a desired velocity and/or acceleration, into a command output, such as a force or torque, for producing the desired motion.

In various exemplary embodiments, an inverse model can be used for model sections 630, 632. An inverse model may be implemented by receiving a desired behavior, such as, for example, a desired motion of the patient side cart, as an input and outputting a command to achieve the behavior. In other words, rather than modeling a cart's behavior by receiving a command, such as a force or torque, as an input and outputting a predicted behavior for the cart, such as a velocity and/or acceleration, an inverse model does the reverse.

According to an exemplary embodiment, fore/aft model section 630 can include an inverse model configured to receive a desired fore/aft movement signal 620, which may correspond to a desired velocity and/or acceleration, and output a fore/aft command output 640, which may represent a force or a torque, based on the modeled fore/aft behavior for a patient side cart. The output fore/aft command output 640 may then be received by, for example, a motor, which interprets the output/fore aft command output 640 signal and drives a driven wheel on the basis of the command output 640. Similarly, yaw model section 632 can include an inverse model configured to receive a desired yaw rate signal 622, which may correspond to a desired velocity and/or acceleration, and output a yaw rate command output 642, which may represent a force or a torque, based on the modeled fore/aft behavior for a patient side cart. The output yaw rate command output 642 may then be received by, for example, one or more motors, which interpret the yaw rate aft command output 642 signal and drive one or more driven wheels on the basis of the command output 640 to turn a patient side cart.

Figure 7:
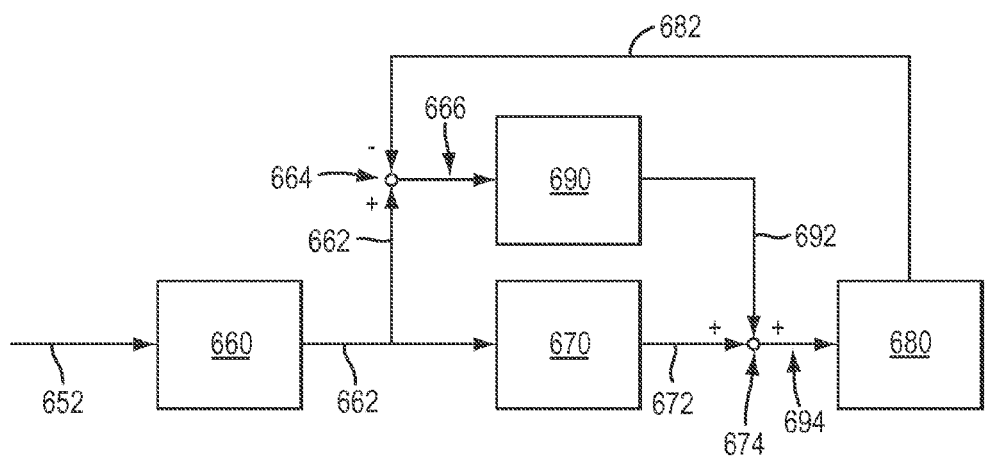
FIG. 7 is a schematic block diagram of an exemplary embodiment of a control system for a patient side cart that includes feedback control.

To provide a drive system that is relatively accurate and stable, in various exemplary embodiments, a control system may include a feedback control that measures the motion of a patient side cart and feeds information about the motion of the cart back into the control system. Turning to FIG. 7, an exemplary embodiment of a control system including feedback control is shown. The control system of FIG. 7 may, for example, be used as the control system 540 of FIG. 5. As shown in FIG. 7, an input signal 652 may be provided to a control module 660 of the control system that produces a desired movement signal 662. Input signal 652 may correspond to signals $F_x$, $F_y$ of FIG. 6, control module 660 may correspond to control modules 610, 612 of FIG. 6, and desired movement signal 662 may correspond to desired movement signals 620, 622 of FIG. 6. According to an exemplary embodiment, control module 660 and a model section 670 may be arranged in a feed forward arrangement, with desired movement signal 662 fed to model section 670. The desired movement signal 662 is received by model section 670, which produces a command output 672 that is sent to a driven component 680 of a patient side cart to cause the desired movement. A driven component 680 may be a driven wheel of a patient side cart, such as one of front wheels. 410, 412 shown in FIG. 3. Model section 670 may correspond to model sections 630, 632 of FIG. 6 and command output 672 may correspond to command outputs 640, 642 of FIG. 6.

The feedback portion of a control system can measure the output 682 of the driven component 680, such as a velocity, acceleration, and/or yaw rate. For example, a sensor may be configured to detect the velocity, acceleration, and/or yaw rate of one or more driven wheels or of the cart as a whole. For instance, a sensor may be configured to detect a driven wheel rotational velocity (or the angle, which can be used to derive the rotational velocity). The output 682 may then be fed back and compared to a desired movement signal 662 produced by the control module 660, such as at an error detector 664.

If the error detector 664 determines that the output 682 and the desired movement signal 662 differ, an error signal or output 666 is provided that is indicative that the patient side cart is not moving as desired. The error output 666 is input to a feedback control module 690. The error output 666 may represent a difference between the output 682 and the desired movement signal 662. The feedback control module 690 may generate a feedback command output 692 that is combined with the command output 672, such as at an adder 674. Feedback command output 692 and command output 672 may be combined to produce a corrected command output 694 that is provided to the driven component 680 to provide a more accurate and stable control of the movement of a patient side cart.

According to an exemplary embodiment, a patient side cart may include feedback control for each of fore/aft movement and yaw rate control. As discussed above, providing feedback control may provide more accurate and stable controls for a patient side cart. These advantages may be provided for each of the fore/aft and yaw components of a patient side cart's movements.

Figure 8:
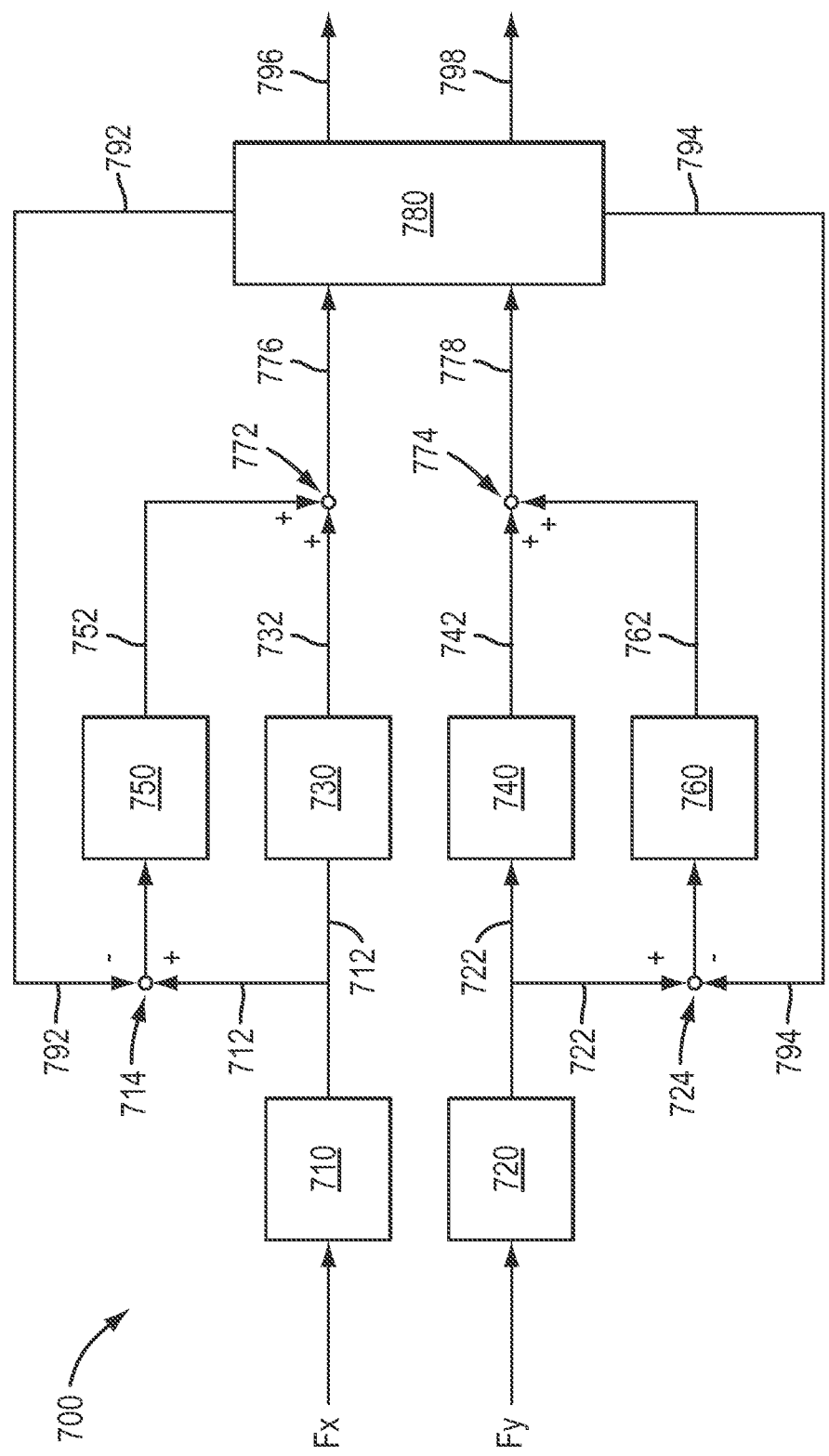
FIG. 8 is a schematic block diagram of another exemplary embodiment of a control system for a patient side cart that includes feedback control.

Referring now to FIG. 8, a schematic block diagram is shown for an exemplary embodiment of a control system 700 for a patient side cart that includes feedback control for fore/aft movement and yaw rate control. As shown in FIG. 8, the control system 700 receives one or more input signals, such as $F_x$, $F_y$, as discussed above in reference to FIG. 6. A first control module 710, which may correspond to control module 610 of FIG. 6, may receive input signal $F_x$ and output a desired fore/aft movement signal 712. A fore/aft model section 730, which may correspond to fore/aft model section 630 of FIG. 6, may receive the desired fore/aft movement signal 712 and output a fore/aft command output 732. Similarly, a second control module 720, which may correspond to control module 612 of FIG. 6, may receive input signal $F_y$ and output a desired yaw rate signal 722 to a yaw rate model section 740, which may correspond to yaw model 632 of FIG. 6, which issues a yaw rate command output 742.

To provide specific command outputs to individual driven wheels of a patient side cart, control system 700 may include a cart dynamics section 780 configured to receive fore/aft command output 732 and yaw rate command output 742 and issue command outputs for individual wheels that will cause a patient side cart to move in the fore/aft direction and turn at the desired yaw rate. For instance, cart dynamics section 780 may analyze the fore/aft command output 732 and the yaw rate command output 742 and issue a left driven wheel torque command output 796 and a right driven wheel torque command output 798. According to an exemplary embodiment, command outputs may be provided to motors that driven the driven wheels of a patient side cart. According to an embodiment, left driven wheel torque command output 796 may be issued for a left front wheel of a patient side cart, such as to the motor for the left front wheel 410 of FIG. 4, and right driven wheel torque command output 798 may be issued for a right front wheel of a cart, such as to the motor for the right front wheel 412 of FIG. 3.

Left driven wheel torque command output 796 and a right driven wheel torque command output 798 may be the same or may differ. For instance, if the force applied by a user to a steering interface indicates a desire to move a patient side cart forwards or backwards along a straight line, such as along the X direction of FIG. 3, the left driven wheel torque command output 796 and a right driven wheel torque command output 798 may be the same to cause a left front wheel and a right front to have the same torque and rotate at the same rate.

However, if the force applied by a user to a steering interface indicates a desire to turn a patient side cart, such as in a direction having a Y direction component as shown in FIG. 3, the left driven wheel torque command output 796 and a right driven wheel torque command output 798 may differ so that the left front wheel and the right front wheel rotate at different rates, which may cause a torque that turns a patient side cart at the desired yaw rate. By configuring a drive system of a patient side cart to turn the cart by turning driven wheels at different speeds, the cart may be advantageously permitted to pivot about a point located between the driven wheels. This may provide smoother, tighter turning in comparison to a cart that pivots about a point located outside (not between) the driven wheels of the cart.

To provide feedback control, output signals may be provided from cart dynamics section 780 and fed back within the control system 700. For instance, cart dynamics section 780 may provide a fore/aft output signal 792 and a yaw rate output signal 794. As shown in FIG. 8, fore/aft output signal 792 may be compared with the desired fore/aft movement signal 712, such as at error detector 714, and yaw rate output signal 794 may be compared with the desired yaw rate signal 722, such as at error detector 724. Any differences resulting from the comparison at error detectors 714, 724 are sent to feedback control modules 750, 760, respectively. Fore/aft feedback control module 750 may be configured to produce a fore/aft feedback command output 752, which is combined with the fore/aft command output 732, such as at adder 772, to provide a corrected fore/aft command output 776, which is in turn sent to cart dynamics section 780. Yaw feedback control module 760 may be configured to produce a yaw rate feedback command output 762, which is combined with the yaw rate command output 742, such as at adder 774, to provide a corrected yaw rate command output 778, which is in turn sent to cart dynamics section 780.

A patient side cart may include features or embodiments in addition to those discussed above. For example, although it is desired that a drive system of a patient side cart will provide motive force to move the cart so that minimal effort will be required from a user, it may be desirable for the drive system to not provide all of the force necessary to move the cart in a desired manner. According to an exemplary embodiment, the drive system of a patient side cart may provide the majority of the force necessary to move the cart but require a user to provide a small degree of the force. In this way, the user may feel the mass and handling of the cart when pushing or pulling the cart. Thus, the user may understand how massive the cart may be and how smoothly the cart moves so the user may appreciate the care that should be used when moving the cart. According to an embodiment, a control system of a patient side cart may include one or more filters to affect the command outputs issued to the driven wheels of the cart, such as by reducing the amount of torque applied to the wheels or by reducing a desired velocity or acceleration for the driven wheels.

According to an exemplary embodiment, a patient side cart may include one or more safety devices to cut power for the drive system when a patient side cart is not being moved. For example, a steering interface may include one or more "dead man" switches, as discussed in U.S. application Ser. No. 14/208,663, filed on Mar. 13, 2014 and claiming priority to U.S. Provisional Application No. 61/791,924 entitled "Surgical Patient Side Cart with Steering Interface" and filed on Mar. 15, 2013, each of which is incorporated by reference herein in its entirety. Thus, when a user is not applying a sufficient force to a steering interface, the steering interface may stop providing a signal from the "dead man" switch. When such a signal is no longer received by the drive system of a patient side cart, the drive system may be configured to cease power to driven wheels to stop movement of the cart. In addition, a patient side cart may include a manual brake control or an emergency kill switch for a user to cut power to the cart.

When the "dead man" switch is released, the drive system of a cart may be configured to bring the cart to an immediate stop, according to an exemplary embodiment. For instance, the drive system may apply brakes to bring the cart to an immediate stop. According to an exemplary embodiment, a brake mechanism may be configured to brake a driven wheel of a cart, such as, for example, one or both of front wheels. 410, 412 of the exemplary embodiment of FIG. 3. However, the exemplary embodiments described herein are not limited to braking only driven wheels of a cart. According to an exemplary embodiment, a brake mechanism may be configured to brake a non-driven wheel of a cart, such as, for example, one or both of non-driven rear wheels 420 of the exemplary embodiment of FIG. 3. According to another exemplary embodiment, both driven wheels and non-driven wheels may be braked.

In one exemplary embodiment, braking can be accomplished by a brake mechanism alone without any use of motors to decelerate a cart, such as the motors 411, 413 of the exemplary embodiment of FIG. 3. According to another exemplary embodiment, a cart may be gradually decelerated once a "dead man" switch has been released to bring the cart to a smoother stop, in comparison to when braking is immediately applied upon release of the "dead man" switch. For instance, one or more motors may be used to gradually decelerate a cart over a period of time, such as by applying a negative torque to wheels connected to the motors. In another exemplary embodiment, if the drive wheels are pivotable, directions of the drive wheels could be changed in a pair-wise manner so that the drive wheels oppose each other, thus increasing friction to achieve deceleration. The period of deceleration may depend, for example, upon the speed of the cart at the time the "dead man" switch is released. In various exemplary embodiments, the period of deceleration may increase as the speed of the cart increases. The cart speed used to determine the period of deceleration may be, for example, an actual cart speed or a target cart speed at the time the "dead man" is released. Once the period of deceleration has passed, brakes may be applied to bring the cart to a stop.

In another exemplary embodiment, the brakes of a cart may be configured to apply a variable braking force. For example, the brakes can apply a first, lower level of braking force during the period of deceleration and then apply a second, higher level of braking force to bring the cart to a stop once the period of deceleration has ended.

According to an exemplary embodiment, the "dead man" switch may be used to overcome a fault status for a patient side cart to permit the cart to be moved. A fault may occur, for example, when a problem occurs with a drive motor, which may cause the brakes of the cart to be automatically engaged to minimize or prevent further movement of the cart while the cart has a fault status. The "dead man" switch may be depressed by a user to disengage the brakes to place the cart in a neutral, "free-wheeling" state that permits a user to push the cart to a different location, even when the cart has a fault status. According to an exemplary embodiment, when the cart is in a neutral, free-wheeling state, motor windings may be opened to prevent electromechanical braking, which may otherwise result if the windings were closed. According to an exemplary embodiment, if the "dead man" switch is released before the fault condition is cleared, the brakes of the cart are reengaged. If the "dead man" switch is depressed by a user at the same time when a fault condition occurs, the controls may be configured to sense release of the "dead man" switch followed by re-depression of the switch to cause disengagement of the brakes.

A "dead man" switch may have various levels of sensitivity corresponding to differing actions performed by a patient side cart, according to an exemplary embodiment. For instance, when the "dead man" switch is not depressed, power is not supplied to the drive system of the cart. When the "dead man" switch is depressed by application of a first amount of force, the cart functions normally and the brakes of the cart are not engaged. When the "dead man" switch is depressed by application of a second amount of force greater than the first amount of force, the cart may be deactivated, such as by cutting power to the drive system of the cart. According to an exemplary embodiment, the second amount of force may correspond to a situation in which a user firmly grasps a handle of the cart when the user is alarmed, such as due to a flight or fight response. Because the user is alarmed and reacts by grasping the handle even more firmly, rather than releasing the handle, the cart would not otherwise be deactivated (such as when the "dead man" switch is released). Thus, making the "dead man" switch sensitive to the second, higher amount of pressure permits the drive system of a cart to be disengaged when a user presses the "dead man" switch with the second, higher amount of force, such as when the user is alarmed and grasps a handle of the cart more firmly.

Figure 9:
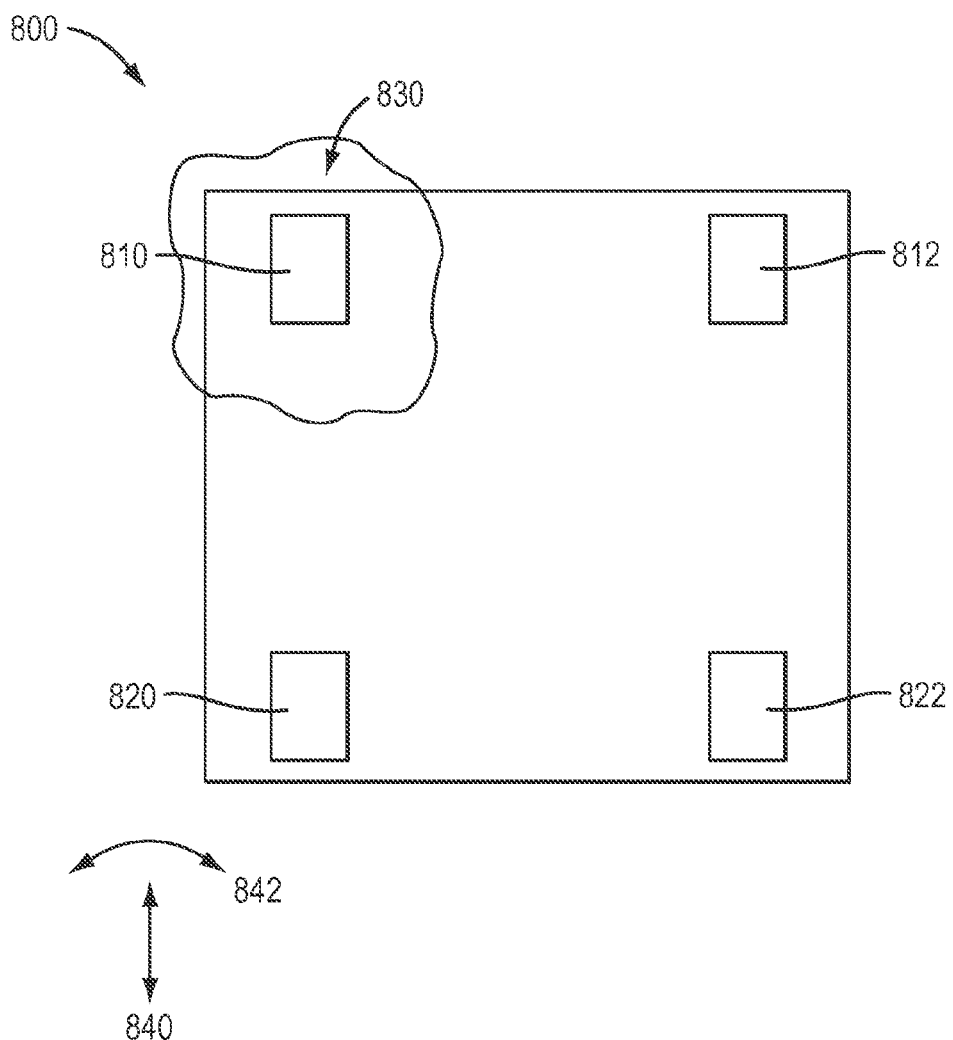
FIG. 9 is a plan schematic view of an exemplary embodiment of a wheel arrangement of a patient side cart.

According to an exemplary embodiment, the drive system of a patient side cart may include traction control. During movement of a patient side cart, one or more wheels of the cart may lose traction with a ground surface, such as when the ground surface is slippery or when inertial loads during movement of the cart or when traversing hills of various slopes in various directions, resulting in a transfer of weight from one wheel to another. When the drive system of a cart includes traction control, the cart may respond to traction loss by changing commands to drive motors for wheels so that motion of cart corresponds to a motion desired by a user to a greater degree, in comparison to when the cart is experiencing a loss of traction. For instance, when a particular wheel loses traction, the speed of the contact surface for that particular wheel relative to the ground may become non-zero. According to an exemplary embodiment, a drive system of a cart may respond to a loss of traction for a particular wheel by reducing the driving or braking torque applied to that particular wheel. Turning to FIG. 9, a top schematic view of an exemplary embodiment of a wheel arrangement for a patient side cart 800 is shown, includes driven front wheels 810, 812 and rear wheels 820, 822. In the exemplary embodiment of FIG. 9, driven front wheel 810 has encountered a low friction region 830 of a ground surface, resulting in a loss of traction for front wheel 810. In response to the loss of traction for front wheel 810, a drive system of a cart may reduce the magnitude of the torque for front wheel 810 to reduce slip between front wheel 810 and the ground surface. The direction of the torque for front wheel 810 may be either positive (e.g., for acceleration) or negative (e.g., for deceleration). According to an exemplary embodiment, the torque for driven front wheel 812 may also be adjusted, which may result in a reduction in the control of cart 800 in a fore/aft direction 840 but enhancement of the control of cart 800 in a yaw direction 842. In other words, control of cart 800 in fore/aft direction 840 may be sacrificed via traction control so that cart 800 may be controlled in yaw direction 842. For instance, if only wheels 810, 812 are driven and wheel 810 loses traction, virtually only one degree of freedom may remain for controlling the motion of cart 800 via driven wheel 812. Thus, a drive system for cart 800 may be configured to control the motion of cart 800 in yaw direction 842, such as by adjusting the torque for wheel 812, instead of controlling the motion of cart in fore/aft direction 840 while wheel 810 lacks traction.

According to an exemplary embodiment, a drive system of a patient side cart (such as the drive system 500 of the exemplary embodiment of FIG. 5 and a drive system including the control systems of the exemplary embodiments of FIGS. 6-8) may include one or more devices to determine when a loss of traction occurs. For instance, traction loss may be detected by a sensor, such as, for example, a yaw rate sensor. According to another exemplary embodiment, traction loss may be determined by a model of the dynamics of a patient side cart and a model of the dynamics of the stand-alone wheel. For instance, one model may provide the behavior of the cart when a loss of traction occurs between one or more wheels, such as one or more driven wheels, and a ground surface and another model may provide the behavior of the cart when no slip occurs, which may also be used to correct the behavior of the cart when there is a loss of traction. According to an exemplary embodiment, when a drive system of a cart uses speed control (e.g., commands the cart to move at a certain speed), the drive system could analyze the input for a particular wheel to determine if the drive command is below a predetermined threshold indicating a loss of traction. The input to be analyzed may be, for example, the inertia, torque, and/or power of the wheel. When speed control is used for a cart and a wheel of the cart loses traction, the input for that wheel likely decreases as the drive system maintains a desired speed of the cart. Thus, the drive system may analyze inputs for the various wheels of a cart to determine whether the input has diminished below a predetermined threshold. According to another exemplary embodiment, a drive system may analyze an input to determine if the input is below a predetermined threshold for a predetermined amount of time to determine when a loss of traction is occurring.

According to an exemplary embodiment, a drive system may determine the inertia of a wheel to determine whether a loss of traction is occurring. For instance, by knowing a wheel torque and an acceleration of a wheel, one may determine the inertia of a wheel. When a wheel of a cart has lost traction with a ground surface, the inertia of the wheel is relatively low because the inertia is substantially that of just the wheel. Conversely, the inertia is higher when the wheel has traction with the ground surface because the measured inertia is not only that of the wheel but also at a least a portion of the cart. A drive system of a cart may determine whether the inertia is lower than a predetermined inertia threshold. When the inertia is lower than the threshold, the drive system determines that the wheel has lost traction and enacts yaw control. According to an exemplary embodiment, the drive system may repeat its determination of wheel inertia and compare the inertia to the threshold, continuing to enact yaw control until the drive system determines that the inertia is greater than the threshold, which indicates that traction has been restored.

According to an exemplary embodiment instead of using a predetermined inertia threshold and enacting traction control if a wheel inertia falls below the threshold, a drive system may implement a continuum for motion control. For instance, once inertia has been determined for a wheel, a drive system may determine where the determined wheel inertia falls on a continuum ranging from a small inertia, which may correspond to a wheel that lacks traction, to a large inertia, which may correspond to a cart wheel having traction. The drive system may then use a control value corresponding to where the wheel inertia falls on the spectrum when using traction control. Thus, the traction control utilizing a continuum may be sensitive to the amount of slipping and control movement according to the amount of slipping.

According to another embodiment, a patient side cart may include a kick plate. As shown in the exemplary embodiment of FIG. 2, a kick plate 320 having a sensor may be located at the rear of a patient side cart, e.g., the side of the cart where the steering interface is located. A steering interface 300 may be designed according to a situation when a user is pushing off of a ground surface to apply a force to the steering interface 300. However, if a user puts a foot on the back of a patient side cart in an attempt to help move the cart forward, while simultaneously holding the steering interface 300, there may be a tendency to pull back on the steering interface in the X (aft) direction. In this situation, since the force applied to the steering interface 300 is in the X (aft) direction, the cart would move backward in the aft direction toward the user, even though the user is attempting to move the cart forward by using the user's foot. To prevent this situation, the kick plate 320 can be configured to send a signal to stop power to drive the cart when a user engages or strikes the kick plate 320. For a further explanation regarding an embodiment of a kick plate that can be used, reference is made to U.S. application Ser. No. 14/208,663, filed on Mar. 13, 2014 and claiming priority to U.S. Provisional Application No. 61/791,924 entitled "Surgical Patient Side Cart with Steering Interface" and filed on Mar. 15, 2013.

According to an exemplary embodiment, a patient side cart may include a system to prevent or minimize collisions between the cart and other objects. For example, a patient side cart may include radar or a light detection and ranging (LIDAR) system that detects objects in the path of the cart and issues a signal to the control system of the cart warning of a possible collision, which may cause the cart to stop.

According to an exemplary embodiment, the drive system also may be configured to adjust the wheels of a patient side cart to permit the cart to move in sideways manner. For instance, driven wheels 410, 412 in FIG. 3 may be rotated left or right ninety degrees (e.g., from theft position shown in FIG. 3) and locked into that orientation so that cart 400 may be permitted to move only sideways along the Y direction. According to an exemplary embodiment, such a rotation of wheels may be actuated by a control located on the steering interface of a patient side cart. Because wheels 420, 422 may be free to rotate, wheels 420, 422 will follow the movement of wheels 410, 412. Such a configuration may permit a patient side cart to enter relatively tight spots and move in a manner that would be otherwise difficult by turning cart via driven wheels 410, 412 as discussed above. In this mode of transportation, force on the steering interface 400 in the Y direction will cause sideways movement either to the left or the right depending on the direction the force is exerted on the steering interface 400 in the Y direction.

By providing a patient side cart with a drive system, the relatively large weight of the cart may be moved without requiring the user to provide the force necessary to move the patient side cart without the drive system. Further, the drive system may include a relatively accurate and stable control system that uses modeled behavior of the cart and feedback control.

Exemplary embodiments, including the various operational methods described herein, can be implemented in computing hardware (computing apparatus) and/or software, such as (in a non-limiting example) any computer that can store, retrieve, process and/or output data and/or communicate with other computers. The results produced can be displayed on a display of the computing hardware. One or more programs/software comprising algorithms to affect the various responses and signal processing in accordance with various exemplary embodiments of the present disclosure can be implemented by a processor, such as data interface module, of or in conjunction with the control cart including core processor and may be recorded on computer-readable media including computer-readable recording and/or storage media. Examples of the computer-readable recording media include a magnetic recording apparatus, an optical disk, a magneto-optical disk, and/or a semiconductor memory (for example, RAM, ROM, etc.). Examples of the magnetic recording apparatus include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limitina, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with a true scope and spirit being indicated by the following claims.

What is claimed is:

1. A teleoperated surgical system cart, the cart comprising:
    a base;
    a surgical instrument support structure extending from the base, the surgical instrument support structure being adjustable to different configurations, the surgical instrument support structure being configured to be removably coupled with a surgical instrument;
    a steering interface configured to be grasped by a user;
    a sensor mechanism configured to detect a force applied to the steering interface; and
    a drive system comprising:
        a control module operably coupled to receive an input from the sensor mechanism in response to the force applied to the steering interface and information about a configuration of the surgical instrument support structure, the control module being programmed with a model correlating the received input from the sensor mechanism and the information about the configuration of the surgical instrument support structure with a movement output command, the control module being configured to output the movement output command in response to the received input from the sensor mechanism and in response to the received information about the configuration of the surgical instrument support structure; and
        a driven wheel mounted to the base and configured to impart wheeled motion to the cart in response to the movement output command.

2. The cart of claim 1, wherein the surgical instrument support structure is adjustable to at least a stowed configuration and an extended configuration.

3. The cart of claim 2, wherein the movement output command comprises a command to control a drive system parameter within a first range when the surgical instrument support structure is in the extended configuration and a command to control the drive system parameter within a second range different from the first range when the surgical instrument support structure is in the stowed configuration.

4. The cart of claim 3, wherein the drive system parameter is chosen from velocity and acceleration of the cart.

5. The cart of claim 4, wherein the first range and the second range comprise respective maximum values of the drive system parameter chosen from velocity and acceleration, the maximum value of the second range being larger than the maximum value of the first range.

6. The cart of claim 4, wherein the surgical instrument support structure is adjustable through a range of partially extended configurations between the stowed configuration and the extended configuration.

7. The cart of claim 6, wherein the movement output command comprises a command to control the drive system parameter within a third range of values of the drive system parameter chosen from velocity and acceleration, the third range having a maximum value between the maximum value of the first range and the maximum value of the second range.

8. The cart of claim 7, wherein the maximum value of the third range of values of the drive system parameter chosen from velocity and acceleration varies over the range of partially extended configurations of the surgical instrument support structure.

9. The cart of claim 1, further comprising a sensor configured to sense a configuration of the surgical instrument support structure, the control module being operably coupled to the sensor to receive information about the configuration of the surgical instrument support structure from the sensor.

10. The cart of claim 9, wherein the sensor comprises at least one of a proximity sensor and a position encoder.

11. The cart of claim 1, further comprising a sensor configured to detect a speed of the driven wheel of the cart, the control module being operably coupled to the sensor to receive detected speed of the driven wheel from the sensor, the model further correlating the movement output command with the speed of the driven wheel.

12. The cart of claim 1, wherein the surgical instrument support structure comprises a jointed arm.

13. The cart of claim 12, wherein the surgical instrument support structure comprises a telescoping post extending from the base, the jointed arm extending from the telescoping post.

14. A method of controlling movement of a teleoperated surgical system cart, the cart comprising a surgical instrument support structure configured to support a surgical instrument, the method comprising:
    detecting a force applied to a steering interface of the cart;
    receiving at a control module of the cart an input corresponding to the force applied to the steering interface of the cart;
    outputting a movement command from the control module, the movement command being based on a model correlating the received input and a configuration of the surgical instrument support structure of the cart with the movement command; and
    moving a driven wheel of the cart to move the cart based on the movement command.

15. The method of claim 14, wherein outputting the movement command comprises controlling a drive parameter of the driven wheel within a first range of values when the surgical instrument support structure is in a stowed configuration and controlling the drive parameter within a second range of values when the surgical instrument support structure is in an extended configuration.

16. The method of claim 15, wherein controlling the drive parameter of the driven wheel comprises controlling a drive parameter chosen from velocity and acceleration of the cart.

17. The method of claim 16, further comprising controlling the drive parameter of the driven wheel within a third range of values of the drive parameter chosen from the velocity and acceleration of the cart when the surgical instrument support structure is within a range of partially extended configurations between the stowed configuration and the extended configuration.

18. The method of claim 17, wherein the third range of values of the drive parameter chosen from velocity and acceleration of the cart includes a third maximum value between a first maximum value of the first range and a second maximum value of the second range.

19. The method of claim 18, wherein the third maximum value of the drive parameter chosen from velocity and acceleration of the cart varies over the range of partially extended configurations of the surgical instrument support structure.

* * * * *